(12) United States Patent
Harris

(10) Patent No.: US 7,875,433 B2
(45) Date of Patent: Jan. 25, 2011

(54) COMPARATIVE MULTIPLE ANALYTE ASSAY

(75) Inventor: Paul C. Harris, Bothell, WA (US)

(73) Assignee: Response Biomedical Corporation, Burnaby, British Columbia (CA)

( * ) Notice: Subject to any disclaimer, the term of this patent is extended or adjusted under 35 U.S.C. 154(b) by 303 days.

(21) Appl. No.: 12/070,353

(22) Filed: Feb. 15, 2008

(65) Prior Publication Data
US 2008/0206889 A1 Aug. 28, 2008

Related U.S. Application Data

(60) Provisional application No. 60/903,474, filed on Feb. 26, 2007.

(51) Int. Cl.
G01N 33/53 (2006.01)

(52) U.S. Cl. .................... 435/7.1; 435/4; 435/7.94; 435/287.1; 435/287.2; 435/287.7; 435/810; 435/970; 435/975; 436/514; 436/518; 436/808; 436/810

(58) Field of Classification Search ............... 435/7.1, 435/4, 7.94, 287.1, 287.2, 287.7, 810, 970, 435/975; 436/514, 518, 808, 810
See application file for complete search history.

(56) References Cited

U.S. PATENT DOCUMENTS

| | | | |
|---|---|---|---|
| 4,361,537 A | 11/1982 | Deutsch et al. | |
| 5,141,850 A | 8/1992 | Cole et al. | |
| 5,236,826 A | 8/1993 | Marshall | |
| 5,356,782 A | 10/1994 | Moorman et al. | |
| 5,384,264 A | 1/1995 | Chen et al. | |
| 5,415,994 A | 5/1995 | Imrich et al. | |
| 5,424,220 A * | 6/1995 | Goerlach-Graw et al. | ... 436/518 |
| 5,458,852 A | 10/1995 | Buechler | |
| 5,506,114 A | 4/1996 | Sangha | |
| 5,569,589 A | 10/1996 | Hiraoka et al. | |
| 5,569,608 A | 10/1996 | Sommer | |
| 5,602,040 A | 2/1997 | May et al. | |
| 5,610,077 A | 3/1997 | Davis et al. | |
| 5,622,871 A | 4/1997 | May et al. | |
| 5,648,274 A | 7/1997 | Chandler | |
| 5,656,503 A | 8/1997 | May et al. | |
| 5,753,517 A | 5/1998 | Brooks et al. | |
| 5,780,251 A | 7/1998 | Klainer et al. | |
| 5,851,048 A | 12/1998 | Fujita et al. | |
| 5,885,527 A | 3/1999 | Buechler | |
| 5,935,780 A | 8/1999 | Naser | |
| 6,103,536 A | 8/2000 | Geisberg | |
| 6,121,008 A | 9/2000 | Fitzpatrick et al. | |
| 6,133,048 A | 10/2000 | Penfold et al. | |
| 6,136,610 A | 10/2000 | Polito et al. | |
| 6,187,598 B1 | 2/2001 | May et al. | |
| 6,228,660 B1 | 5/2001 | May et al. | |
| 6,436,721 B1 * | 8/2002 | Kuo et al. | ............ 436/514 |
| 6,482,362 B1 * | 11/2002 | Smith | ............ 422/100 |
| 7,175,992 B2 | 2/2007 | Fong | |
| 2002/0082386 A1 | 6/2002 | Mangold et al. | |
| 2004/0235189 A1 | 11/2004 | Lu | |
| 2006/0240541 A1 | 10/2006 | Petruno et al. | |

FOREIGN PATENT DOCUMENTS

| | | |
|---|---|---|
| EP | 0 093 613 | 11/1983 |
| EP | 0 250 137 A2 | 12/1987 |
| EP | 0 462 376 A2 | 12/1991 |
| EP | 0 464 376 A2 | 12/1991 |
| EP | 1 003 037 B1 | 11/2001 |
| EP | 0 896 223 B1 | 9/2003 |
| EP | 1 361 435 A1 | 11/2003 |
| EP | 1 550 872 A2 | 7/2005 |
| GB | 2 235 292 A | 2/1991 |
| WO | WO 87/06345 | 10/1987 |
| WO | WO 93/03175 | 2/1993 |
| WO | WO 97/09620 | 3/1997 |
| WO | WO 88/08534 | 11/1998 |
| WO | WO 99/35602 | 7/1999 |
| WO | WO 99/36780 | 7/1999 |
| WO | WO 01/50129 A2 | 7/2001 |
| WO | WO 03/016575 A1 | 2/2003 |
| WO | WO 2006/083367 A2 | 8/2006 |

(Continued)

OTHER PUBLICATIONS

Reeves, S.G. and Durst, R.A., "Novel Optical Measurement Approach for the Quantification of Liposome Immunomigration Assays," *Analytical Letters*, 28(13): 2347-2362 (1995).

(Continued)

Primary Examiner—Bao-Thuy L Nguyen
(74) Attorney, Agent, or Firm—Hamilton, Brook, Smith & Reynolds, P.C.

(57) ABSTRACT

Methods for measuring the relative amount of two or more analytes of interest in a fluid sample, as well as kits useful in the methods, are disclosed. The methods involve assays that utilize a solid phase apparatus with a membrane having an application point and at least two sample capture zones having sample capture reagents; analyte binding particles or analyte coated particles; and assessment of a ratio of such particles arrested in capture zones, wherein the ratio is equal to, or inversely equal to, the relative amounts of the analytes of interest in the fluid sample.

9 Claims, No Drawings

FOREIGN PATENT DOCUMENTS

WO  WO 2007/024633 A2  3/2007

OTHER PUBLICATIONS

Borque, L., et al., "Automated Quantitative Nephelometric Latex Immunoassay for Determining Ferritin in Human Serum," *J. Clin. Lab. Analysis*, 6: 239-244 (1992).

Roberts, M.A. and Durst, R.A., Investigation of Liposome-Based Immunomigration Sensors for the Detection of Polychlorinated Biphenyls,: *Analytical Chem*. 67:482-491 (1995).

Siebert, S.T.A., et al., Lipsome Immunomigration Field Assay Device for Alachlor Determination, *Analytica Chimica Acta*, 282:297-305 (1993).

Siebert, R.S., et al., "Improved Liposome Immunomigration Strip Assay for Alachlor Determination," *Analytica Chimica Acta*, 311:309-318(1995).

Schifreen, R.S., et al., "A Quantitative Automated Immunoassay for Fibrinogen/Fibrin Degradation Products," *Clin. Chem.*, 31(9): 1468-1473 (1985).

Laitinen, M.P.A. and Vuento, M., "Immunochromatographic Assay for Quantitation of Milk Progesterone," *Acta Chemica Scandinavica*, 50:141-145 (1996).

Findlay, J.W.A., et al., "Validation of Immunoassays for Bioanalysis: a Pharmaceutical Industry Perspective," *Journal of Pharmaceutical and Biomedical Analysis*, 21(6): 1249-1273 (2000).

Paek, S.H., et al., "Development of Rapid One-Step Immunochromatographic Assay," *Methods*, 22(1): 53-60 (2000).

Fitzpatrick, J. et al., "7C Gold Urinary Assay of Neural Thread Protein in Alzheimer's Disease," *Alzheimer's Reports*, 3: 155-159 (2000).

* cited by examiner

COMPARATIVE MULTIPLE ANALYTE ASSAY

RELATED APPLICATION

This application claims the benefit of U.S. Provisional Application No. 60/903,474, filed on Feb. 26, 2007. The entire teachings of the above application are incorporated herein by reference.

BACKGROUND OF THE INVENTION

Analysis of cells and analytes in fluid samples, particularly bodily fluid samples, often provides critical diagnostic and treatment information for physicians and patients. Immunoassays utilize the specificity of the antigen (Ag)—antibody (Ab) reaction to detect an Ag or Ab in a sample. In solid phase immunoassays, one reagent (e.g., the Ag or Ab) is attached to a solid surface, facilitating separation of bound reagents or analytes from free reagents or analytes. The solid phase is exposed to a sample containing the analyte, which binds to its Ag or Ab; the presence of this binding is indicative of the presence of the analyte in the sample, and extent of this binding can be quantitated to provide a measure of the analyte concentration in the sample. Transduction of the binding event into a measurable signal, however, is affected by a number of limitations, including constraints of particle movement on the solid phase and background signal, which affect the specificity and applicability of immunoassays. In addition, related analytes of interest may compete or otherwise interfere with one another in an assay, rendering it difficult to assess correctly the presence of more than one analyte of interest.

SUMMARY OF THE INVENTION

The invention relates to methods of measuring the relative amount of two or more analytes of interest in a fluid sample, using an assay, such as solid phase assay (e.g., a sandwich immunoassay or an inhibition immunoassay), in which an analyte of interest and a capture reagent are used as part of a specific binding pair; and to kits for use in the methods.

In representative methods of the invention, a solid phase apparatus such as a lateral flow solid phase apparatus or a capillary flow solid phase apparatus, is provided. The solid phase apparatus includes an application point and two or more sample capture zones (one corresponding to each analyte of interest); the sample capture zones can be, for example, sequentially located on the membrane, or approximately equidistant from the application point. A sample capture reagent (e.g., an agent that binds to the analyte of interest, such as an antibody to the analyte of interest) is adsorbed at each of the sample capture zones; one for each analyte of interest. In certain embodiments, a sample collection apparatus is provided, in which the sample collection apparatus contains population(s) of particles, such as liposomes, colloidal gold, or organic polymer latex particles, stored in a stable form. In certain other embodiments, the population(s) of particles is adsorbed on a conjugate zone or zones of the membrane, wherein the conjugate zone is, for example, positioned at the application point, or a conjugate zone is positioned sequentially between the application point and the first sample capture zone when sample capture zones are sequentially located, or positioned sequentially between the application point and each sample capture zone when the sample capture zones are approximately equidistant from the application point.

In sandwich assays of the invention, the particles are analyte binding particles that are coated with a binding agent (e.g., an antibody) to each of the analytes of interest; alternatively, different populations of analyte binding particles, each coated with a binding agent to one of the analytes of interest, are utilized. In competitive or inhibition assays, the particles are "analyte coated" particles that are coated with analytes of interest or analog(s) of the analytes of interest; alternatively, different populations of analyte coated particles, each coated with one of the analytes of interest, are utilized. In either type of assay, the particles can be labeled, using a colorimetric, fluorescent, luminescent, chemiluminescent, or other appropriate label, to facilitate detection.

In one embodiment of the methods, a fluid sample to be assessed for two or more analytes of interest is introduced into the sample collection apparatus, and a buffer is subsequently introduced into the mixed fluid sample. In another embodiment of the methods, a buffer is introduced into the sample collection apparatus, and the fluid sample to be assessed for the analytes of interest is subsequently introduced. In a third embodiment of the methods, the fluid sample is formed by introducing a solid into a buffer, and the fluid sample is subsequently introduced into the sample collection apparatus. In any of these embodiments, a buffered, mixed fluid sample containing the particles is produced. The buffered, mixed fluid sample is applied to the application point of the membrane of the solid phase apparatus. In another embodiment of the methods, the fluid sample is not introduced into a sample collection apparatus, but is applied to the application point of the solid phase apparatus, and then moves by capillary action through conjugate zone(s).

In a sandwich assay, analytes of interest present in the sample interact with the analyte binding particles (whether in the sample collection apparatus or on the conjugate zone), resulting in contacted analyte binding particles. The solid phase apparatus is then maintained under conditions which are sufficient to allow capillary action of fluid to transport particles to and through the sample capture zones. The sample capture reagent interacts with contacted analyte binding particles, resulting in arrest of particles in the sample capture zones.

The relative amount of analyte binding particles that are arrested in each sample capture zone, can then be assessed, for example, as a ratio of the amount of analyte binding particles that are arrested in a first sample capture zone to the amount of analyte binding particles that are arrested in a second sample capture zone.

In a competitive or inhibition type of assay, the fluid sample is also applied to the application point of the solid phase apparatus. The solid phase apparatus is then maintained under conditions which are sufficient to allow capillary action of fluid to transport analyte coated particles to and through conjugate zone(s), if present, and to and through the sample capture zones. The sample capture reagents interact with analyte coated particles; interaction of sample capture reagents and analyte coated particles results in arrest of analyte coated particles in the sample capture zones. Because of competition between the analyte coated particles and analyte (if present) in the sample for binding sites on the sample capture reagents in the sample capture zones, the amount of analyte coated particles arrested in the sample capture zones is inversely proportional to the amount of the analytes in the sample. The amount of analyte coated particles that are arrested in the sample capture zones are then determined, for example, as a ratio of the amount of analyte coated particles that are arrested in a first sample capture zone, to the amount of analyte coated particles that are arrested in a second sample capture zone.

If desired, a background amount of particles can be subtracted from the amount of analyte binding particles or analyte coated particles arrested in each sample capture zone, before determination of the ratios.

In an additional embodiment of the invention, the assay is conducted in the absence of a solid phase apparatus. In this embodiment, a sample collection apparatus containing a population of first analyte binding particles and a population of second analyte binding particles, is used. A buffered, mixed fluid sample comprising contacted first analyte binding particles and contacted second analyte binding particles is prepared, and then contacted with a first sample capture reagent that binds to contacted first analyte binding particles, and with a second sample capture reagent that binds to contacted second analyte binding particles. The ratio of the amount of first analyte binding particles captured by the first capture reagent, to the amount of second analyte binding particles captured by the second capture reagent, can then be determined.

In a further embodiment of the invention, the assay is conducted using a solid phase apparatus other than a lateral flow solid phase apparatus or a capillary flow solid phase apparatus (e.g., using a microtiter plate as the solid phase apparatus). In this embodiment, a sample collection apparatus containing a population of first analyte binding particles and a population of second analyte binding particles, is used. A buffered, mixed fluid sample comprising contacted first analyte binding particles and contacted second analyte binding particles is prepared, and then contacted with a solid phase apparatus having adsorbed thereon at distinct locations, a first sample capture reagent that binds to contacted first analyte binding particles, and with a second sample capture reagent that binds to contacted second analyte binding particles. The ratio of the amount of first analyte binding particles captured by the first capture reagent, to the amount of second analyte binding particles captured by the second capture reagent, can then be determined.

The methods of the invention provide simple, highly accurate assessment of relative amounts of analytes, without need for internal controls.

DETAILED DESCRIPTION OF THE INVENTION

The present invention pertains to methods of assessing the relative amount of two or more analytes of interest, and kits therefor.

An assay, as used herein, refers to an in vitro procedure for analysis of a sample to determine the relative quantity of analytes. The assays of the inventions utilize at least two analytes of interest and analyte binding agents that correspond to the analytes of interest. Each analyte of interest and its analyte binding agent are members of a specific binding pair, in which a first member of the binding pair (e.g., analyte) reacts specifically with a second member (e.g., the binding agent). One or both members of the binding pair can be an antibody. For example, a first member of the binding pair (e.g., an analyte of interest) can be an antibody, and a second member of the binding pair (e.g., a binding agent) can be anti-immunoglobulin antibody; alternatively, the first member of the binding pair (e.g., the analyte) can be an antigen, and the second member of the binding pair (e.g., the binding agent) can be an antibody.

In one embodiment, the assay is an immunoassay which utilizes antibodies as a component of the procedure. In one preferred embodiment, the immunoassay is a sandwich assay, which is a test for analytes in which a fluid sample to be assessed for the relative quantity of analytes is contacted with particles coated with an analyte binding agent, such as antibodies to one or both of the analytes, and the resultant mixture is applied to a solid phase apparatus and subsequently moves by capillary action through the apparatus. In another preferred embodiment, the immunoassay is an inhibition or competitive assay, which is a test for analytes in which a fluid test sample to be assessed for the relative quantity of analytes, is contacted with particles coated with one or both of the analytes, and the resultant mixture is applied to a solid phase apparatus and subsequently moves by capillary action through the apparatus. In additional embodiments, the assays do not employ a solid phase apparatus, but are conducted solely in solution.

In other embodiments of the assays of the invention, neither an analyte nor its binding agent in a specific binding pair are antibodies: for example, the first member of the binding pair can be a ligand, and the second member of the binding pair can be a receptor; alternatively, the first member of the binding pair can be a lectin, and the second member of the binding pair can be a sugar. In still another embodiment, the first member of the binding pair can be a nucleic acid (e.g., DNA, RNA), and the second member of the binding pair can be a nucleic acid which specifically hybridizes to the first member of the binding pair. Specific hybridization, as used herein, refers to the ability of a first nucleic acid to hybridize to a second nucleic acid in a manner such that the first nucleic acid does not hybridize to any nucleic acid other than to the second nucleic acid (e.g., when the first nucleic acid has a higher similarity to the second nucleic acid than to any other nucleic acid in a sample wherein the hybridization is to be performed). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 80%, 85%, 90%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in *Current Protocols in Molecular Biology* (Ausubel, F. M. et al., *Current Protocols in Molecular Biology*, John Wiley & Sons, (1998), the entire teachings of which are incorporated by reference herein). The exact conditions which determine the stringency of hybridization depend not only on ionic strength (e.g., 0.2× SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules.

Regardless of the composition of an analyte and its binding agent, these two components nevertheless form a specific binding pair, in which the first member reacts specifically with the second member. Specific interaction between the members of the binding pair indicates that the first member of the binding pair preferentially binds or otherwise interacts with the second member of the binding pair, preferably to the exclusion of any binding to another compound in the assay.

The terms, analyte or analyte of interest, as used herein, refer to a first member of a binding pair as described above. The analyte is a molecule or compound for which the amount will be measured. The analyte can be in the form of a solid, such as a dry substance (e.g., a powder, a particulate; spore; or other particle), or can be in the form of a fluid (e.g., a solid as described above that has been dissolved or suspended in a fluid; or other liquid sample). Examples of analytes include bacteria; spores; proteins, such as hormones or enzymes; glycoproteins; peptides; small molecules; polysaccharides; antibodies; nucleic acids; drugs; toxins (e.g., environmental toxins); viruses or virus particles; portions of a cell wall; and other compounds. In a preferred embodiment, each analyte is "immunogenic," which indicates that antibodies (as described below) can be raised to that analyte, or to analyte that is bound to a carrier (e.g., a hapten-carrier conjugate, for which antibodies can be raised to the hapten). In some representative embodiments, a first analyte of interest can be HDL cholesterol and a second analyte of interest can be LDL cholesterol; or a first analyte of interest can be placental growth factor (PlGF) and the second analyte of interest can be soluble fms-like tyrosine kinase 1 (sFlt-1). In other representative embodiments, a first analyte of interest can be T-3, and a second analyte of interest can be T-4; if desired, an alternative or additional analytes can also include thyroid stimulating hormone (TSH). The analytes of interest can be in a liquid sample; alternatively, the analytes of interest can be in a dry (non-fluid) sample (e.g., a solid, such as a particulate sample, powder sample, or soil sample). Each analyte of interest is a first member of a binding pair as described above—i.e., each analyte of interest reacts specifically with a second member of a binding pair.

An analyte binding agent, as used herein, refers to second member of a binding pair as described above. Each analyte binding agent is a compound that specifically binds to its analyte of interest (the first member of the binding pair), such as an antibody, a hapten or drug conjugate, a receptor, or another binding partner. In a preferred embodiment, an analyte binding agent is an antibody to its analyte of interest.

In the methods of the invention, a fluid sample is assessed for the presence or absence, or quantity, of two or more analytes of interest. The fluid can be a fluid that wets the membrane material (in embodiments utilizing a solid phase comprising a membrane); that supports a reaction between each analyte of interest and its analyte binding agent, such as the antibody/antigen reaction (i.e., does not interfere with antibody/antigen interaction); and that has a viscosity that is sufficiently low to allow movement of the fluid by capillary action. In a preferred embodiment, the fluid is an aqueous solution (such as a bodily fluid). The fluid sample can be a fluid having relatively few components, for example, an aqueous solution containing the analyte of interest; alternatively, the fluid sample can be a fluid having many components, such as a complex environmental sample (e.g., sewage, waste water, groundwater, or other water sample), or a complex biological fluid (e.g., whole blood, plasma, serum, urine, cerebrospinal fluid, saliva, semen, vitreous fluid, synovial fluid, or other biological fluid). In a preferred embodiment in which the fluid is a biological fluid, the fluid is whole blood, plasma, or serum. If desired, the fluid sample can be diluted; for example, if a complex biological fluid is used as the fluid sample, it can be diluted with a buffer or solution (e.g., an aqueous solution).

If one of the analytes of interest is not in solution (e.g., an analyte of interest is in a dry or solid sample, as described above), it can be extracted, suspended, or dissolved into a fluid sample first. For example, if an analyte of interest is a nucleic acid, it can be extracted from cells of interest into a solution (e.g., an aqueous solution, such as the buffer described below); in another example, if an analyte of interest is a powder or particulate material (e.g., a powder, a particulate, a soil sample, or spores), it can be suspended or dissolved into a solution (e.g., an aqueous solution, such as the buffer described below) such as by obtaining a sample of the dry material (e.g., using a swab or other instrument) and placing the sample of dry material into the solution. Thus, a fluid sample can refer not only to a liquid sample to be assessed for an analyte of interest, but also to a fluid sample in which a solid material (to be assessed for an analyte of interest) is extracted, suspended or dissolved.

Sandwich Assays

Certain sandwich assays of the invention utilize a solid phase apparatus. In one embodiment, the solid phase apparatus is a lateral flow solid phase apparatus. In the other embodiment, the solid phase apparatus is a capillary flow solid phase apparatus.

The lateral flow solid phase apparatus can be any solid phase apparatus designed for a lateral flow assay, such as the RAMP™ apparatus (Response Biomedical, Burnaby, British Columbia, Canada; see, e.g., apparatus described in U.S. Pat. Nos. 6,509,196; 7,175,992). Generally, the lateral flow solid phase apparatus includes a membrane through which the test sample will flow. The membrane has an application point and two or more sample capture zones. The solid phase apparatus may optionally include a wicking pad following the sample capture zones, and an application pad adjacent to or covering the application point. The membrane can be made of a substance having the following characteristics: sufficient porosity to allow capillary action of fluid along its surface and through its interior; the ability to allow movement of coated particles (e.g., analyte binding particles, as described below) or complexes of particles and analyte of interest (e.g., contacted analyte binding particles, as described below) by capillary action (i.e., it must not block the particles or complexes of particles and analyte of interest); and the ability to be wet by the fluid containing the analytes (e.g., hydrophilicity for aqueous fluids, hydrophobicity for organic solvents). Hydrophobicity of a membrane can be altered to render the membrane hydrophilic for use with aqueous fluid, by processes such as those described in U.S. Pat. No. 4,340,482, or U.S. Pat. No. 4,618,533, which describe transformation of a hydrophobic surface into a hydrophilic surface. Examples of membrane substances include: cellulose, cellulose nitrate, cellulose acetate, glass fiber, nylon, polyelectrolyte ion exchange membrane, acrylic copolymer/nylon, and polyethersulfone. In a preferred embodiment, the membrane is made of cellulose nitrate (e.g., a cellulose nitrate membrane with a Mylar backing).

The capillary flow solid phase apparatus can be any solid phase apparatus designed for a capillary flow assay, such as the BioSite Triage® immunoassay products (BioSite Inc., San Diego, Calif.). Generally, the capillary flow solid phase apparatus includes a capillary channel through which the test sample will flow.

Whether a lateral flow solid phase apparatus or a capillary flow solid phase apparatus is used, the solid phase apparatus has an application point and two or more sample capture zones. The application point (or application area) is the position on the membrane or in the capillary channel where a fluid can be applied. A sample capture zone refers to a point on the membrane or in the capillary channel at which a sample capture reagent is adsorbed (e.g., coated on and/or permeated through the membrane, or coated on the surface of the capillary channel). As used herein, the term "adsorbed" indicates that the agent is immobilized or adhered by non-covalent interactions, in contrast to covalent linkage where chemical means are used to generate an irreversible chemical bond of shared electrons between two linked molecules. Incremental movement (e.g., desorbtion) of an agent that is adsorbed onto a membrane may occur, but will have negligible affect on the assays of the invention.

A sample capture reagent is an analyte binding agent, such as those described above, for a particular analyte of interest. A sample capture reagent need not be the same analyte binding agent as described in relation to analyte binding agents on particles, below; however, each sample capture reagent also forms a binding pair with its analyte of interest, in that it specifically and preferentially binds to its analyte of interest. In a preferred embodiment, a sample capture reagent is an antibody directed against its analyte of interest; it can be directed against the same epitope of the analyte as, or against a different epitope of the analyte from, the epitope that binds to the antibodies used as analyte binding agents coated on the particles. Because there is more than one analyte of interest, there will accordingly be more than one sample capture zone—one sample capture zone corresponding to each analyte of interest. Each sample capture zone has a sample capture reagent adsorbed thereon, in which the sample capture reagent is an analyte binding agent for its particular (corresponding) analyte of interest.

In certain embodiments, the sample capture zones are positioned sequentially with respect to the flow of liquid by capillary action on the membrane or in the capillary channel, and proximal to the application point. In certain other embodiments, the sample capture zones are approximately equidistant from the application point (e.g., parallel to one another, radially dispersed, or otherwise positioned such that the sample capture zones are proximal to the application point with respect to the flow of liquid). If desired, the sample capture zones can be comparatively closer to the distal end of the membrane than to the application point. In a further embodiment, the sample capture zones overlap or occupy the same area; in such an embodiment, the particles used (as described below) are distinctively labeled (i.e., labeled in such a manner that they can be separately identified, such as by differing optical densities, different chemiluminescent markers, and/or different fluorescent markers).

In sequential placement of the sample capture zones in embodiments in which the sample capture zones do not overlap or occupy the same area, the distance between each zone can be varied; all that is required is that the distance is sufficient such that the zones do not overlap. In a preferred embodiment, sequential zones are spaced such that a background level can also be determined between the various zones, as discussed in detail below. In sequential placement of the sample capture zones, each sample capture zone is approximately equidistant from the sample capture zones adjacent to it. The term, "approximately equidistant" indicates that the distance is as close as possible using standard manufacturing equipment: for example, if the manufacturing equipment resolution is a millimeter, approximately equidistant would be within 1 mm. Alternatively, in another particular embodiment, approximately equidistant resolution can be related to the distance from the center of the first sample capture zone to the center of the second capture zone: for example, the difference between the distance from the center of the first sample capture zone to the center of the second sample capture zone and the distance from the center of the second sample capture zone to the center of the third capture zone, is within 10%, preferably within 7%, preferably within 5%, more preferably within 4%, more preferably within 3%, even more preferably within 2%, and even more preferably within 1%, of the length of the distance from the center of the application point to the center of a sample capture zone (the length of the pathway).

The term, "approximately equidistant" is similarly applicable when the sample capture zones are approximately equidistant from the application point. It should be noted that the capillary paths from the application point to each sample capture zone do not cross when each sample capture zone is "approximately equidistant": that is, the path of fluid flow from the application point to each capture zone remains distinct and does not cross over any other path of fluid flow. In contrast, when the sample capture zones are positioned sequentially, there is a single capillary path from the application point to each sample capture zones: that is, there are not overlapping or distinct paths of fluid flow, but rather, the path of fluid flow from the application point to each capture zone is a single path.

The sample capture zones are separated from the application point by a space that is sufficiently large to retard the speed of the capillary front to a rate that is slow enough to allow capture of particles when the capillary front reaches the first sample capture zone. In addition, the distance must be sufficiently large so that the total time of migration (movement of the capillary front through the entire membrane) is long enough to allow free analyte in a fluid sample to bind to analyte binding particles. The optimal distances between the components on the membrane can be determined and adjusted using routine experimentation.

In certain embodiments of the invention, a sample collection apparatus is employed. A sample collection apparatus, as used herein, refers to an apparatus that can be used for collection of the fluid sample or into which a collected fluid sample can be deposited or stored. The sample collection apparatus can be any apparatus which can contain the analyte binding particles, as described below, and which to which can be added a measured volume of fluid sample. Representative sample collection apparatus include a sample tube, a test tube, a vial, a pipette or pipette tip, or a syringe. In a preferred embodiment, the sample collection apparatus is a pipette or pipette tip.

In one embodiment, the sample collection apparatus contains a population of analyte binding particles which are coated with an analyte binding agent for each analyte of interest: for example, a first analyte binding agent for a first analyte of interest; a second analyte binding agent for a second analyte of interest; etc., such that there is an analyte binding agent corresponding to each analyte of interest. Alternatively, the sample collection apparatus can contain a population of analyte binding particles for each analyte binding agent; that is, a population of analyte binding particles for a first analyte of interest; a population of analyte binding particles for a second analyte of interest; etc., such that there is a population of analyte binding particles corresponding to each analyte of interest. If desired a combination of different types of populations of analyte binding particles can also be used.

The population(s) of particles varies, depending on the size and composition of the particles, the composition of the membrane of the solid phase apparatus, and the level of sensitivity of the assay. The population typically ranges approximately between $1 \times 10^3$ and $1 \times 10^9$, although fewer or more can be used if desired. In a preferred embodiment, the population is approximately $2 \times 10^8$ particles. The population may be accordingly increased if desired (e.g., with three times as many particles if three analytes of interest are assessed).

Analyte binding particles are particles which can be coated with the analyte binding agent (the second member of the binding pair) for each analyte of interest. In a preferred embodiment, the analyte binding particles are liposomes, colloidal gold, organic polymer latex particles, inorganic fluorescent particles or phosphorescent particles. In a particularly preferred embodiment, the particles are polystyrene latex beads, and most particularly, polystyrene latex beads that have been prepared in the absence of surfactant, such as surfactant free Superactive Uniform Aldehyde/Sulfate Latexes (Invitrogen., Carlsbad, Calif.).

The size of the particles is related to porosity of the membrane or the width of the capillary channel (for analytes in fluid samples) and also to the size of the analytes of interest (e.g., for particulate analytes): the particles must be sufficiently small to be transported along the membrane or through the capillary channel by capillary action of fluid, and also (for solid, e.g., particulate analytes) sufficiently small for the complex of contacted analyte binding particles, as described below, to be transported along the membrane or through the capillary channel by capillary action. The particles must also be sufficiently large to hold label for detection, and sufficiently large such that weak molecular forces such as Van der Waals or ionic attraction will not cause the particles to stick to surfaces rather than to move by capillary action of fluid. In one embodiment, for example, the particles are at least about 200 nM; in another preferred embodiment, for example, the particles are at least about 300 nM.

The particles can be labeled to facilitate detection. The particles are labeled by a means which does not significantly affect the physical properties of the particles; for example, the particles are labeled internally (that is, the label is included within the particle, such as within the liposome or inside the polystyrene latex bead). Representative labels include luminescent labels; chemiluminescent labels; phosphorescent labels; enzyme-linked labels; chemical labels, such as electroactive agents (e.g., ferrocyanide); and colorimetric labels, such as dyes or fluorescent labels. In one embodiment, a fluorescent label is used. In another embodiment, phosphorescent particles are used, particularly "up-converting" phosphorescent particles, such as those described in U.S. Pat. No. 5,043,265. If the sample capture zones are separate, for example, the same type of label can be used for each population of analyte binding particles (e.g., for both the population of particles for the first analyte of interest, and the population of particles for the second analyte of interest). Alternatively, different types of labels (distinctive labels) can be used, e.g., if the sample capture zones over lap or occupy the same area.

The particles are coated with an analyte binding agent that is a second member of the binding pair for each analyte of interest (e.g., particles having more than one type of analyte binding agent coated thereon; or different populations of particles, each population having a single type of analyte binding agent for its analyte coated thereon). As described above, an analyte binding agent (second member of a binding pair) specifically and preferentially binds to its analyte of interest (first member of the binding pair). Representative analyte binding agents include antibodies (or fragments thereof); haptens; drug conjugates; receptors; or other binding partners. In one preferred embodiment, the analyte binding agent is an antibody to the analyte of interest. Antibodies can be monoclonal antibodies or polyclonal antibodies. The term "antibody", as used herein, also refers to antibody fragments which are sufficient to bind to the analyte of interest.

Alternatively, in another embodiment, molecules which specifically bind to the analyte of interest, such as engineered proteins having analyte binding sites, can also be used (Holliger, P. and H. R. Hoogenbloom, *Trends in Biotechnology* 13:7 9 (1995); Chamow, S. M. and A. Ashkenazi, *Trends in Biotechnology* 14:52 60: 1996)). In still another embodiment, if the analyte of interest is a drug, a hapten or other drug conjugate can be used as the analyte binding agent. Alternatively, in a further embodiment, a receptor which binds to the analyte can be used (e.g., if the analyte of interest is a ligand). If the analyte is an antibody of known specificity, the particles can be coated with the antigen against which the analyte antibody is directed, or can be coated with antibody to the analyte-antibody. Furthermore, because the analyte and the analyte binding agent form a binding pair, compounds or molecules described as representative analytes can also serve as analyte binding agents, and those described as representative analyte binding agents can similarly serve as analytes, as described herein.

The analyte binding particles contained within the sample collection apparatus are stored in a stable form within the sample collection apparatus. A "stable form," as the term is used herein, indicates a form in which the particles do not significantly change in chemical makeup or physical state during storage. The stable form can be a liquid, gel, or solid form. In preferred embodiments, the analyte binding particles contained within the sample collection apparatus are evaporatively dried; freeze-dried; and/or vacuum-dried. In a particularly preferred embodiment, the sample collection apparatus is a pipette tip in which are vacuum-dried analyte binding particles.

To perform the assay utilizing the sample collection apparatus, a fluid sample to be assessed for the presence of the analytes of interest, as described above, is used. In one embodiment, the fluid sample is introduced into (drawn into, poured into, or otherwise placed into) the sample collection apparatus. For example, in one embodiment, the fluid sample is drawn up into a sample collection apparatus that comprises a pipette tip. Introduction of the fluid sample into the sample collection apparatus results in mixing of the fluid sample with the analyte binding particles, forming a "mixed fluid sample." If the analyte binding particles are evaporatively-, freeze- or vacuum-dried, the introduction of the fluid sample into the sample collection apparatus can result in rehydration and suspension of the analyte binding particles in the fluid sample. A buffer (e.g., for dilution) is also introduced into the mixed fluid sample, forming a "buffered, mixed fluid sample." The buffered, mixed fluid sample can be formed either by dispensing the mixed fluid sample into a "buffer container" (e.g., test tube) containing the buffer, or by introducing the buffer into the sample collection apparatus prior to introducing the fluid sample. Alternatively, if the analyte of interest is a solid (e.g., a powder, a particulate; spore; or other particle, as described above), the fluid sample as described above can be prepared by introducing the solid into the buffer container; in this embodiment, the buffered, mixed fluid sample is formed by introducing the fluid sample (comprising the buffer) into the sample collection apparatus. In another embodiment, the buffer is introduced into the sample collection apparatus, followed by introduction of the fluid sample into the sample collection apparatus.

The buffer can be an aqueous fluid that supports a reaction between the analyte of interest and the analyte binding agent (e.g., does not interfere with antibody/antigen interaction); and that has a viscosity that is sufficiently low to allow movement of the fluid by capillary action. In one embodiment, the buffer contains one or more of the following components: a buffering agent (e.g., phosphate); a salt (e.g., NaCl); a protein stabilizer (e.g., BSA, casein, serum); and/or a detergent such as a nonionic detergent or a surfactant (e.g., one or more of the following agents commonly available in surfactant tool kits: NINATE 411, Zonyl FSN 100, Aerosol OT 100%, GEROPON T 77, BIO TERGE AS 40, STANDAPOL ES 1, Tetronic 1307, Surfnyol 465, Surfynol 485, Surfynol 104PG 50, IGEPAL CA210, TRITON X 45, TRITON X 100, TRITON X305, SILWET L7600, RHODASURF ON 870, Cremophor EL, TWEEN 20, TWEEN 80, BRIJ 35, CHEMAL LA 9, Pluronic L64, SURFACTANT 10G, SPAN 60, CREL). Optionally, if desired, the buffer can contain a thickening agent. Such components for buffers are commercially available. Representative buffers include, for example, saline, or 50 mM Tris HCl, pH 7.2. Alternatively, water can be used in lieu of a buffered solution; as used herein, the term "buffer" refers to either a buffered solution or to water. In another embodiment, the components of the buffer are lyophilized and included in the sample collection apparatus; in this embodiment, water is used in lieu of the buffered solution in the methods of the invention.

To disperse the analyte binding particles further into the fluid sample, if desired, the sample collection apparatus into which the fluid sample and the buffer has been introduced, or the buffer container into which the mixed fluid sample has been introduced, can be agitated (e.g., vortexed, shaken, pipetted down and up, etc.).

In a preferred embodiment, the sample collection apparatus comprises a pipette tip having vacuum-dried analyte binding particles within its tip; the fluid sample is drawn into the pipette, thereby rehydrating the dried analyte binding particles and forming a mixed fluid sample. In a particularly preferred embodiment, the mixed fluid sample is introduced into a buffer container, resulting in a buffered mixed fluid sample; the buffered mixed fluid sample in the buffer container is pipetted up and down using the sample collection apparatus, thereby further dispersing the analyte binding particles.

If an analyte of interest is present in the buffered, mixed fluid sample, binding occurs between that analyte and its analyte binding particles. "Binding" of analyte to analyte binding particles indicates that an analyte binding agent coated onto the particle is interacting with (e.g., binding to) its analyte of interest. Analyte binding particles which have been maintained (incubated) under conditions allowing analytes in the fluid (if present) to bind to analyte binding particles adsorbed in the contact region are referred to herein as "contacted analyte binding particles". Contacted analyte binding particles may or may not have analytes bound to the analyte binding agent, depending on whether or not each analyte of interest is present in the fluid sample and whether analyte has bound to the analyte binding agent on the analyte binding particles. Because there are multiple binding sites for analyte on analyte binding particles, the presence and the concentration of analyte bound to analyte binding particles varies; the concentration of an analyte bound to analyte binding particles increases proportionally with the amount of analyte present in the fluid sample, and the probability of an analyte binding particle being arrested in the corresponding sample capture zone (as described below) similarly increases with increasing amount of analyte bound to the analyte binding particles. Thus, the population of contacted analyte binding particles may comprise particles having various amount of analytes bound to the analyte binding agents, as well as particles having no analytes bound to the analyte binding agents (just as the analyte binding particles initially have no analyte bound to the analyte binding agent). Furthermore, the degree of binding increases as the time factor of the conditions increases: while the majority of binding occurs within one minute (e.g., 60 seconds, preferably less than 60 seconds (e.g., 45 seconds, 30 seconds, or less), additional incubation (e.g., more than one minute (2 minutes, 5 minutes, 10 minutes, 15 minutes) results in additional binding. If there is more than one population of analyte binding particles (e.g., separate populations for the different analytes of interest), analyte binding particles which have been maintained (incubated) under conditions allowing analytes in the fluid (if present) to bind to the analyte binding particles are referred to as "contacted first analyte binding particles," "contacted second analyte binding particles," etc., for each analyte of interest, and are collectively known as contacted analyte binding particles.

The buffered, mixed fluid sample is applied to the application point of the membrane of the solid phase apparatus, or to the application pad, if present. An application pad can also optionally be used; the application pad rests on the membrane, immediately adjacent to or covering the application point. The application pad can be made of an absorbent substance which can deliver a fluid sample, when applied to the pad, to the application point on the membrane. Representative substances include cellulose, cellulose nitrate, cellulose acetate, nylon, polyelectrolyte ion exchange membrane, acrylic copolymer/nylon, polyethersulfone, or glass fibers. In one embodiment, the pad is a Hemasep®-V pad (Pall Corporation). In another embodiment, the pad is a glass fiber pad. If a wicking pad is present, it can similarly be made from such absorbent substances.

In another embodiment of the invention, the population(s) of analyte-binding particles can be adsorbed on the membrane or in the capillary channel in lieu of being contained in a separate sample collection apparatus. A "conjugate zone," as used herein, refers to a region of the membrane or of the capillary channel at which the population(s) of analyte-binding particles are adsorbed or otherwise attached; alternatively, a "conjugate zone" can be a conjugate pad that is fluid contact with the membrane or capillary channel (e.g., an application pad). Both situations in which the conjugate zone is part of the membrane or capillary channel itself, and in which the conjugate zone is a conjugate pad, are referred to herein as a "conjugation zone". In embodiments in which the sample capture zones are sequentially placed, the conjugate zone is positioned either at the application point itself (such that the application point and the conjugate zone are the same), or at any point between the application point, up to but not overlapping the first sample capture zone. In embodiments in which the sample capture zones are approximately equidistant from the application point, a single conjugate zone is positioned either at the application point itself (such that the application point and the conjugate zone are the same), or multiple conjugate zones are used, with a single conjugate zone downstream between the application point and each sample capture zone. If multiple conjugate zones are used, each contains an approximately equal amount of the population(s) of analyte-binding particles. The conjugate zone should be positioned so that the sample contacts it and mobilizes the particles efficiently and allows sufficient time for analytes to interact with the particles; in general, the conjugate zone is as close to the application point as possible, to allow maximum time for analyte of interest in the fluid sample to interact with particles before capillary flow carries the particles all the way to the sample capture zones.

In embodiments in which a conjugate zone is used, a fluid sample (as described above) is applied directly to the application point of the membrane or the capillary channel of the solid phase apparatus, or to the application pad, if present.

Contacted analyte binding particles are generated as capillary action moves fluid through the conjugate zone(s), when the particles in the conjugate zone(s) interact with analytes (if present) in the fluid sample.

In both the embodiments employing a sample collection apparatus and the embodiments using particles in a conjugate zone, the solid phase apparatus is maintained under conditions which allow fluid to move by capillary action to and through the membrane or the capillary channel. Contacted analyte binding particles move as a result of capillary action of the fluid from the fluid sample, and the contacted analyte binding particles move along the membrane or capillary channel to and through the sample capture zones. The solid phase apparatus is maintained under conditions (e.g., sufficient time and fluid volume) which allow contacted analyte binding particles to move by capillary action to and through the sample capture zones, and subsequently beyond the capture zones (e.g., into a wicking pad), thereby removing any non-bound particles from the capture zones.

The movement of some of the contacted analyte binding particles is arrested by binding of contacted analyte binding particles to the sample capture reagent in the sample capture zone for each analyte of interest. In one preferred embodiment, the analyte binding agents are antibodies to the antigens of interest.

Sample capture reagent binds to contacted analyte binding particles by binding to analyte of interest which is bound to analyte binding agent on the contacted analyte binding particles. The term, sample-reagent particle complexes, as used herein, refers to a complex of sample capture reagent and contacted analyte binding particles. Contacted analyte binding particles are arrested in the sample capture zones, forming the sample-reagent-particle complexes, due to capture of contacted analyte binding particles by interaction of analyte with sample capture reagent in the sample capture zone. Each sample capture zone may have sample-reagent-particle complexes arrested therein, depending on whether each particular analyte of interest is present in the sample and has bound to its analyte binding agent on contacted analyte binding particles.

Capillary action subsequently moves any contacted analyte binding particles that have not been arrested in any sample capture zones onwards beyond these zones, thereby removing any particles that have not been arrested. In a preferred embodiment, the fluid moves any contacted analyte binding particles that have not been arrested, into a wicking pad which follows the last (sequentially) sample capture zone or each (approximately equidistant) sample capture zone.

If desired, a secondary wash step can be used. A buffer (e.g., the buffer described above) can be applied at the application point after the buffered, mixed fluid sample has soaked in to the membrane or into the application pad, if present. The secondary wash step can be used at any time thereafter, provided that it does not dilute the buffered, mixed fluid sample. A secondary wash step can contribute to reduction of background signal when the analyte binding particles are detected, as described below.

The relative amount of analyte binding particles arrested in each sample capture zone (sample-reagent-particle complexes) can then detected using an appropriate means for the type of label used on the analyte binding particles. In a preferred embodiment, the amount is detected by an optical method, such as by measuring the amount of fluorescence of the label of the analyte binding particles. In a particularly preferred embodiment, the entire area from upstream of the first sample capture zone to beyond the last capture zone (or the entire area from upstream of the first sample capture zone to downstream of the first sample capture zone, as well as the entire area from upstream of the second sample capture zone to downstream of the second sample capture zone, etc.) is scanned so that several hundred measurements are taken along the direction of liquid flow. In this manner the amount of binding at each zone and between the zones and before the initial zone and after each zone can be determined with enough resolution to quantitate the amount of label in each of these areas. The amount of binding between the zones can be used to correct for background signal, as described below.

Alternatively, the amount of sample-reagent-particle complexes can be detected using electrical conductivity or dielectric (capacitance). Alternatively, electrochemical detection of released electroactive agents, such as indium, bismuth, gallium or tellurium ions, as described by Hayes et al. (*Analytical Chem.* 66:1860-1865 (1994)) or ferrocyanide as suggested by Roberts and Durst (*Analytical Chem.* 67:482-491 (1995)) can be used. For example, if liposomes are used, ferrocyanide encapsulated within the liposome can be released by addition of a drop of detergent at the capture zone, and the released ferrocyanide detected electrochemically (Roberts and Durst, id.). If chelating agent-protein conjugates are used to chelate metal ions, addition of a drop of acid at the capture zone will release the ions and allow quantitation by anodic stripping voltametry (Hayes et al., id.).

The relative amounts of the analytes of interest can be determined, by determining (for example) the ratio of the amount of contacted analyte binding particles in the first sample capture zone to the amount of contacted analyte binding particles in the second capture zone. For example, in an embodiment in which two populations of analyte binding particles are used to assess the relative amounts of two analytes of interest, a ratio is determined as the amount of the contacted first analyte binding particles in the first sample capture zone, to the amount of the contacted second analyte binding particles in the second sample capture zone. In an embodiment in which a single population of analyte binding particles (e.g., coated with an analyte binding agent for each of the analytes of interest) is used, a ratio is determined as the amount of the contacted analyte binding particles in the first sample capture zone, to the amount of the contacted analyte binding particles in the second sample capture zone. The relative amount of the analytes of interest is equal to the ratio.

If desired, the amount of label that is present in the background can also be subtracted from the analyte binding particle amount present in each sample capture zone prior to calculation of the ratio (R). For example, after the assay is run (liquid has moved through and beyond the capture zones), the whole, or part, of the membrane can be scanned to assess the quantity of labeled particles in the areas before, in, and after each of the capture zones. The scan can be done primarily around the area which includes the capture zones, but can also be performed on the area extending outside and/or between these zones. The particles present in areas outside the capture zones are "background"—that is, particles that bind non-specifically to the membrane in the presence of the sample and other constituents in the sample matrix which are also present at the capture zones. The amount of particles present in the capture zone includes this non-specific background in addition to the specific particles captured by the capture reagent. The detected background amount of particles (i.e., the amount of particles detected in a location outside the capture zone, such as before and/or after that capture zone) can be subtracted from the total amount of particles determined in an individual capture zone. This corrects for background amount, and can yield more accurate determination of the amount of analyte present in the sample. For example, a detected background amount can be identified in a location immediately adjacent and upstream of a capture zone; or in a location immediately adjacent and downstream of a capture zone; or between the application point and the first sample capture zone; or in another location besides the capture zones. Alternatively, a detected background amount can be identified in more than one location: for example, a detected background amount can be identified in a location upstream of a capture zone, and also downstream of the same capture zone; an average of these two detected background amounts can be used as the detected background particle amount that is subtracted from the analyte binding particle amount to yield the "background-corrected analyte binding particle amount." A "background-corrected analyte binding particle amount," as used herein, refers to an analyte binding particle amount from which a background amount of particles has been subtracted.

In a preferred embodiment, the detected background particle amount is determined immediately adjacent and upstream of each individual capture zone: for example, in an embodiment in which there are two analytes of interest and thus two sample capture zones, the background amount is detected upstream of the first sample capture zone (for the first sample capture zone), and downstream of the first sample capture zone and upstream of the second sample capture zone (for the second sample capture zone). Alternatively, the same detected background amount can be used for each of the sample capture zones.

In another preferred embodiment, a detected background particle amount is determined both immediately adjacent and upstream of each individual capture zone, as well as immediately adjacent and downstream of each individual capture zone, and an average of the two amounts is used in the determination of the background-corrected analyte binding particle amount. For example, in an embodiment in which there are two analytes of interest and thus two sample capture zones, the background amount is detected upstream of the first sample capture zone and downstream of the first sample capture zone, and these two amounts are averaged and used as the background amount for the first sample capture zone; the background amount that is downstream of the first sample capture zone is also used as a background amount that is upstream of the second sample capture zone, and it is averaged with a background amount that is downstream of the second sample capture zone, so that the average can be used as the background amount for the second sample capture zone; etc. Other combinations of readings can be used and averaged to serve as the background amount, if desired.

"Competitive" or "Inhibition" Assays

The competitive or inhibition assay of the invention, like the sandwich assays, utilizes a solid phase apparatus, as described above, that includes an application point and two or more sample capture zones. The solid phase apparatus may optionally include a wicking pad(s), and a sample pad preceding the application point. This embodiment can also utilize a sample collection apparatus, as described above, or can use a population of particles at a conjugate zone. The particles used for the competitive (inhibition) assay are "analyte coated particles." In certain embodiments, these particles can be coated with all of the analytes of interest (in lieu of being coated with an analyte binding agents, as described for the sandwich assays) or with analogs of all of the analyte of interest; alternatively, more than one population of analyte coated particles (with one population for each analyte of interest) can be used, in which each population is coated with an analyte of interest or with an analog of an analyte of interest. An analog of the analyte, as used herein, is a compound that has similar binding characteristics as the analyte, in that is forms a binding pair with the analyte-binding agent as described above. The analyte or analog of the analyte can be coated directly on the particles, or can be indirectly bound to the particles. As used below, the term analyte coated particles can refer to particles that are coated either with an analyte of interest or with an analog of an analyte of interest. As above with regard to the sandwich assay, the population of particles varies, depending on the size and composition of the particles, the composition of the membrane of the solid phase apparatus, and the level of sensitivity of the assay.

As above, the sample capture zones are locations on the solid phase apparatus at which a sample capture reagent is adsorbed. The sample capture reagent is an analyte binding agent, such as those described above. The sample capture reagent need not be the same analyte binding agent as described above; however, the sample capture reagent also forms a binding pair with the analyte of interest, in that it specifically and preferentially binds to an analyte of interest. Because there is more than one analyte of interest, there will be more than one sample capture zone, as above. As above, in a preferred embodiment, the sample capture reagent is an antibody directed against the analyte; it can be directed against the same epitope of the analyte as, or against a different epitope of the analyte from, the epitope that binds to the antibodies used as analyte binding agents coated on the particles.

To perform the competitive assay, a fluid sample to be assessed for the presence of the analytes of interest, as described above, is used. In embodiments in which a sample collection apparatus is used, the fluid sample is introduced into (drawn into, poured into, or otherwise placed into) the sample collection apparatus. For example, in one embodiment, the fluid sample is drawn up into a sample collection apparatus that comprises a pipette tip. Introduction of the fluid sample into the sample collection apparatus results in mixing of the fluid sample with the analyte coated particles, forming a mixed fluid sample. If the analyte coated particles are evaporatively-, freeze- or vacuum-dried, the introduction of the fluid sample into the sample collection apparatus can result in rehydration and suspension of the analyte binding particles in the fluid sample. A buffer (e.g., as described above) is also introduced into the mixed fluid sample, forming a buffered, mixed fluid sample. The buffered, mixed fluid sample can be formed either by dispensing the mixed fluid sample into a buffer container (e.g., test tube) containing the buffer, or by introducing the buffer into the sample collection apparatus prior to introducing the fluid sample. In another embodiment, the buffer is introduced into the sample collection apparatus, followed by introduction of the fluid sample into the sample collection apparatus. Alternatively, if analyte of interest is a solid (e.g., a powder, a particulate; spore; or other particle, as described above), the fluid sample as described above can be prepared by introducing the solid into the buffer container; in this embodiment, the buffered, mixed fluid sample is formed by introducing the fluid sample (comprising the buffer) into the sample collection apparatus.

To disperse the analyte coated particles further into the fluid sample, if desired, the sample collection apparatus into which the fluid sample and the buffer has been introduced, or the buffer container into which the mixed fluid sample has been introduced, can be agitated (e.g., vortexed, shaken, pipetted down and up, etc.).

In a preferred embodiment, the sample collection apparatus comprises a pipette tip having vacuum-dried analyte coated particles within its tip; the fluid sample is drawn into the pipette, thereby rehydrating the dried analyte coated particles and forming a mixed fluid sample. In a particularly preferred embodiment, the mixed fluid sample is introduced into a buffer container, resulting in a buffered mixed fluid sample; the buffered mixed fluid sample in the buffer container is pipetted up and down using the sample collection apparatus, thereby further dispersing the analyte coated particles. The fluid sample is applied to the application point of the membrane of the solid phase apparatus, or to the application pad, if present.

In embodiments in which a conjugate zone (having population(s) of analyte contacted particles thereon) is employed, the fluid sample (as described above) is applied directly to the application point of the solid phase apparatus, or to the application pad, if present. Contacted analyte coated particles are generated as capillary action moves fluid through the conjugate zone(s), as the particles of the conjugate zone(s) interact with analytes present in the fluid sample.

After the solid phase apparatus is contacted with the fluid sample, the membrane is maintained under conditions which allow fluid to move by capillary action to and through the solid phase apparatus. The analyte coated particles (and analyte, if present in the sample) move as a result of capillary action of the fluid from the buffered, mixed fluid sample, to and through the sample capture zones. The solid phase apparatus is maintained under conditions (e.g., sufficient time and fluid volume) which allow the analyte coated particles to move by capillary action to and through the sample capture zones, and subsequently beyond the capture zones (e.g., into a wicking pad), thereby removing any non-bound particles from the capture zones.

The movement of some of the analyte coated particles is arrested by binding of analyte coated particles to the sample capture reagent in the sample capture zones. The analyte coated particles compete with analyte (if present) in the sample for binding to the sample capture reagent. The sample capture reagent binds to analyte coated particles by binding to analyte on the analyte coated particles. The term, sample-reagent-analyte coated particle complexes, as used herein, refers to a complex of the sample capture reagent and analyte coated particles. The analyte coated particles can be arrested in a sample capture zone, forming the sample-reagent-analyte coated-particle complexes, due to capture of the analyte coated particles by interaction of the analyte of interest on the particles with the sample capture reagent in the sample capture zone.

Capillary action subsequently moves any analyte coated particles that have not been arrested in a sample capture zone onwards beyond the capture zones. In a preferred embodiment, the fluid moves any contacted analyte coated particles that have not been arrested in a capture zone into a wicking pad.

The analyte coated particles arrested in each capture zone is then detected. The analyte coated particles are detected using an appropriate means for the type of label used on the analyte coated particles, as is described above in relation to detection of amounts of analyte binding particles in the sandwich assay.

The relative amounts of the analytes of interest can be determined, by determining (for example) the ratio of the amount of contacted analyte coated particles in the first sample capture zone to the amount of contacted analyte coated particles in the second capture zone. For example, in an embodiment in which two populations of analyte coated particles are used to assess the relative amounts of two analytes of interest, a ratio is determined as the amount of the contacted first analyte coated particles in the first sample capture zone, to the amount of the contacted second analyte coated particles in the second sample capture zone. In an embodiment in which a single population of analyte coated particles (e.g., coated with both analytes, or analogs of both analytes, or a combination thereof for each of the analytes of interest) is used, a ratio is determined as the amount of the contacted analyte coated particles in the first sample capture zone, to the amount of the contacted analyte coated particles in the second sample capture zone. The relative amount of the analytes of interest is the inverse of the ratio.

In addition, if desired, the amount of label that is present in the background can be subtracted from the analyte coated particle amount present in each sample capture zone prior to calculation of the ratio (R), as described above in relation to sandwich assays. For example, a detected background amount can be identified in a location immediately adjacent and upstream of a capture zone; or in a location immediately adjacent and downstream of a capture zone; or between the application point and the first sample capture zone; or in another location besides the capture zones. Alternatively, a detected background amount can be identified in more than one location: for example, a detected background amount can be identified in a location upstream of a capture zone, and also downstream of the same capture zone; an average of these two detected background amounts can be used as the detected background particle amount that is subtracted from the analyte coated particle amount to yield the "background-corrected analyte coated particle amount." A "background-corrected coated binding particle amount," as used herein, refers to an analyte coated particle amount from which a background amount of particles has been subtracted.

In a preferred embodiment, the detected background particle amount is determined immediately adjacent and upstream of each individual capture zone: for example, in an embodiment in which there are two analytes of interest and thus two sample capture zones, the background amount is detected upstream of the first sample capture zone (for the first sample capture zone); and downstream of the first sample capture zone and upstream of the second sample capture zone (for the second sample capture zone). Alternatively, the same detected background amount can be used for each of the sample capture zones. In another preferred embodiment, a detected background particle amount is determined both immediately adjacent and upstream of each individual capture zone, as well as immediately adjacent and downstream of each individual capture zone, and an average of the two amounts is used in the determination of the background-corrected analyte coated particle amount. For example, in an embodiment in which there are two analytes of interest and thus two sample capture zones, the background amount is detected upstream of the first sample capture zone and downstream of the first sample capture zone, and these two amounts are averaged and used as the background amount for the first sample capture zone; the background amount that is downstream of the first sample capture zone is also used as a background amount that is upstream of the second sample capture zone, and it is averaged with a background amount that is downstream of the second sample capture zone, so that the average can be used as the background amount for the second sample capture zone; etc. Other combinations of readings can be used and averaged to serve as the background amount, if desired.

ADDITIONAL EMBODIMENTS

Additional Analytes

Although the assays described above have been exemplified by assays for two analytes of interest, more analytes can be assessed if desired. In such methods of the invention, the solid phase apparatus includes one sample capture zone corresponding to each and every analyte of interest (e.g., 3, 4, or more sample capture zones); the sample capture zones can be either sequentially located on the solid phase apparatus, or approximately equidistant from the application point (or a combination thereof). As before, a sample capture reagent (e.g., an agent that binds to the analyte of interest, such as an antibody to the analyte of interest) is adsorbed in each of the sample capture zones; one for each analyte of interest.

In embodiments in which a sample collection apparatus is used, the sample collection apparatus contains population(s) of particles. For sandwich immunoassays, the particles are analyte binding particles that are coated with a binding agent to every one of the analytes of interest, or different populations of analyte binding particles, each coated with a binding agent to one of the analytes of interest, are utilized, such that there is one population for each analyte of interest. Alternatively, various populations can be used, some having binding agent to a single analyte of interest, and others having binding agent to more than one analyte of interest. In competitive or inhibition assays, the particles are "analyte coated" particles that are coated with analytes of interest or analog(s) of the analytes of interest for every analyte of interest, or different populations of analyte coated particles, each coated with one of the analytes of interest, are utilized such that there is one population for each analyte of interest. Alternatively, various populations can be used, some having analyte and/or analog of analyte for a single analyte of interest, and others having analyte and/or analog of analyte for more than one analyte of interest.

In certain other embodiments, the population(s) of particles is adsorbed on a conjugate zone or zones of the solid phase apparatus, wherein the conjugate zone is either at the application point, or a conjugate zone is positioned sequentially between the application point and the first sample capture zone when sample capture zones are sequentially located, or positioned sequentially between the application point and each sample capture zone when the sample capture zones are approximately equidistant from the application point. Thus, there may be as few as one conjugate zone, or as many conjugate zones as there are analytes of interest.

In embodiments in which a sample collection apparatus is used for the fluid sample to be assessed for the multiple analytes of interest, the buffered, mixed fluid sample applied to the application point; in embodiments using conjugate zone(s), the fluid sample of interest is applied to the application point of the membrane, and then moves by capillary action through conjugate zone(s).

As described above, analytes of interest present in the sample interact with the analyte binding particles (whether in the sample collection apparatus or on the conjugate zone), resulting in contacted analyte binding particles. The solid phase apparatus is maintained under conditions which are sufficient to allow capillary action of fluid to transport particles to and through the sample capture zones. The sample capture reagent interacts with contacted analyte binding particles, resulting in arrest of particles in the sample capture zones. Capillary action of the fluid continues to mobilize the remaining unbound particles past the sample capture zones (e.g., into a wicking pad). The relative amount of analyte binding particles that are arrested in each sample capture zone, can then be assessed, for example, as a ratio of the amount of analyte binding particles that are arrested in a first sample capture zone, to the amount of analyte binding particles that are arrested in a second sample capture zone, or to the amount of analyte binding particles that are arrested in a third or fourth (etc.) sample capture zone. The relative amounts of analyte binding particles for any of the analytes of interest can be compared (e.g., for three analytes of interest, the first and second, the first and third, or the second and third, can be compared.) If desired, the amount of analyte binding particles for one analyte can be compared to the sum of the amount of analyte binding particles for two or more other analytes.

In a competitive or inhibition type of assay, the fluid sample is also applied to the application point of the solid phase apparatus. The solid phase apparatus is then maintained under conditions which are sufficient to allow capillary action of fluid to transport analyte coated particles to and through the conjugate zones (if present), and to and through the sample capture zones. The sample capture reagents interact with analyte coated particles; interaction of sample capture reagents and analyte coated particles results in arrest of analyte coated particles in the sample capture zones. Because of competition between the analyte coated particles and analyte (if present) in the sample for binding sites on the sample capture reagents in the sample capture zones, the amount of analyte coated particles arrested in the sample capture zones is inversely proportional to the amount of the analytes in the sample. Capillary action of the fluid continues to mobilize the remaining unbound particles past the sample capture zones (e.g., into a wicking pad). The amount of analyte coated particles that are arrested in the sample capture zones are then determined, for example, as a ratio of the amount of analyte coated particles that are arrested in a first sample capture zone, to the amount of analyte coated particles that are arrested in a second sample capture zone, or to the amount of analyte coated particles that are arrested in a third or fourth (etc.) sample capture zone. The relative amounts of analyte coated particles for any of the analytes of interest can be compared (e.g., for three analytes of interest, the first and second, the first and third, or the second and third, can be compared.) If desired, the amount of analyte coated particles for one analyte can be compared to the sum of the amount of analyte coated particles for two or more other analytes.

If desired, a background amount of particles can be subtracted from the amount of analyte binding particles or analyte coated particles arrested in each sample capture zone, before determination of the ratios, as described in detail above.

Combination with Quantitative Assays

In addition, the assays described above can also be combined with quantitative assays (e.g., as described in U.S. Pat. No. 7,175,992). For example, the solid phase apparatus can be designed to assess both relative amounts of certain analytes, as described herein, and also to quantitate specific amounts of other analytes. In a representative embodiment, the apparatus is prepared such that one portion comprises a first and a second sample capture zone sequentially located on the membrane for a first and a second analyte, and another portion comprises a third sample capture zone located essentially equidistant from the application point as one of the first or second sample capture zones. The third sample capture zone forms part of a quantitative assay as described in U.S. Pat. No. 7,175,992. Using this combination assay, a ratio can be determined for the first and second analytes, and a quantitative assessment can be performed for the third analyte. In one preferred embodiment, the analytes are all related to the same condition: for example, diagnosis of pre-eclampsia is made by assessing the sFlt-1/PlGF ratio in a serum sample from a pregnant woman; an assessment of the quantity of B-type natriuretic peptide (BNP) or NT-proBNP also facilitates diagnosis of pre-eclampsia (see, e.g., Grunson, D., "New Biomarkers to Screen the Risk of Pre-eclampsia," International Federation of Clinical Chemistry and Laboratory Medicine, Oct. 24, 2006). The present invention can be used to assess both the sFlt-1/PIGF ratio and the quantity of BNP, using a single sample.

Alternatively, if desired, the third analyte can, in fact, be the same as the first analyte, so that not only a ratio of the first and second analyte can be determined, but also a precise quantity of the first analyte can be determined. This further allows accurate determination of the quantity of the second analyte, using the quantity of the first analyte and the ratio.

Sample Capture Zone Positioning

In addition, the assays of the invention have been described particularly with embodiments in which the sample capture zones are separate (i.e., sequential or equidistant from the application point); however, if desired the sample capture zones can occupy the same area of the membrane. In such embodiments, different populations of particles are used for each analyte of interest, and the populations are labeled so as to be distinguishable (distinctive) from one another. For example, for two analytes in a sandwich assay as described herein, a population of first analyte binding particles (or analyte coated particles) can be labeled with a red fluorescent marker, and a population of second analyte binding particles (or analyte coated particles) can be labeled with a blue fluorescent marker. Background amounts can also be subtracted from the amount of particles arrested in the sample capture zone for this embodiment, if desired.

Assays Utilizing Other Solid Phase Apparatus

In another alternative embodiment of the invention, a solid phase such as a microtiter plate can be used. In one embodiment, the first sample capture reagent and the second sample reagent are adsorbed or located in different zones of the solid phase. For example, the first sample capture reagent can be adsorbed in a first well of the microtiter plate, and the second sample capture reagent can be adsorbed in a second well of the microtiter plate. The first and second analyte binding particles are detectably labeled; if desired, they can also be distinctively labeled as described above. The ratio can be determined, for example, by assessing the signal of the label for each well and determining the ratio accordingly.

Assays in the Absence of a Solid Phase

Although the present invention has been described above with regard to the use of a solid phase apparatus, the invention can similarly be performed without a solid phase apparatus (i.e., in solution). For example, in one alternative embodiment of the invention, the first and second sample capture reagents are not adsorbed to any solid phase, and the ratio can be determined in the fluid sample. In these particular embodiments, a means is used to separate labeled, bound material from labeled, unbound material or otherwise identify labeled, bound material distinctly from unbound material. In certain embodiments, the first and second analyte binding particles are distinctively labeled (i.e., labeled in such a manner that they can be separately identified, such as by differing optical densities, different chemiluminescent markers, and/or different fluorescent markers). Alternatively, a homogeneous detection means can be used to identify the analyte binding particles that are bound to analyte. Representative means include energy transfer means, energy quenching means, chemiluminescent means, enzyme-based means, fluorescence polarization, fluorescent quenching, and other methods. Using these methods, the ratio of the amount of captured first analyte binding particles and captured second analyte binding particles can be determined without a need to capture particles on a solid phase.

Benefits of the Invention

The methods of the invention provide extremely accurate comparison of the relative amounts of analytes of interest. The analyte binding particles or analyte coated particles for each of the analytes are subjected to the same internal conditions during the assay, and assessment of the relative amount of the analytes eliminates the need for an internal control such as that described in U.S. Pat. No. 7,175,992. Also, a ratio of the amount one analyte of interest to the amount another analyte of interest is a particularly valuable tool for diagnostics in which the comparative amounts of the analytes, rather than the absolute amounts of the analytes, are important. For example, as described above, diagnosis of pre-eclampsia is facilitated by assessing the sFlt-1/PIGF ratio in a serum sample from a pregnant woman. The present assay allows easy determination of that ratio and eliminates concerns regarding differing conditions for tests of the individual analytes. Furthermore, the methods of the invention eliminate introduction of errors that may occur when a determination of the ratio of analytes is performed by first determining the concentrations of the analytes by interpolation from standard curves. Standard curves have several associated errors, including errors that occur during the experimental determination of the curves and during interpolation. The comparison of relative amounts of analytes in the methods of the invention avoids these problems.

Kits of the Invention

The invention also includes kits for use in the methods described herein. Kit components can include: first and/or second members of a specific binding pair, buffers and/or buffer containers, fluid collection means, one or more solid phase apparatus (optionally comprising an application pad and/or wicking pad), at least one sample collection apparatus, one or more buffer containers, control samples for generation of a standard curve and/or other standard curve information, analyte binding particles, analyte coated particles, capture reagents, antibodies, tools to assist in collecting of samples to be assessed for analyte of interest (e.g., swabs), disposal apparatus (e.g., biohazard waste bags), and/or other information or instructions regarding the sample collection apparatus (e.g., lot information, expiration date, etc.). For example, in one embodiment, a kit comprises at least one sample collection apparatus having analyte binding particles within it; in a preferred embodiment, a kit comprises at least one pipette tip having evaporatively-dried, vacuum-dried or freeze-dried analyte binding particles therein. In another embodiment, a kit comprises at least one solid phase apparatus as described herein and at least one sample collection apparatus. In another preferred embodiment, a kit comprises at least one pipette; at least one or more pipette tips having evaporatively-dried, vacuum-dried or freeze-dried analyte binding particles therein; and at least one solid phase apparatus. This preferred embodiment can also optionally contain information regarding the standard curve, lot information, and/or expiration date relating to the analyte binding particles in the pipette tips. In yet another preferred embodiment, a kit comprises at least one sample collection apparatus; at least one pipette tip having dried analyte binding particles thereon; at least one solid phase apparatus; and at least one buffer container. This preferred embodiment can also optionally contain buffer within the buffer container; and tool (e.g., a swab) for collection of a solid sample.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining a relative amount of at least two analytes of interest in a fluid test sample, comprising:
   a) providing a solid phase apparatus comprising an application point and at least two sample capture zones, the first sample capture zone having a first sample capture reagent adsorbed thereon and the second sample capture zone having a second sample capture reagent adsorbed thereon;
   b) providing analyte binding particles, wherein the analyte binding particles comprise either: i) a population of first analyte binding particles and a population of second analyte binding particles, wherein the first analyte binding particles are coated with a first analyte binding agent and the second analyte binding particles are coated with a second analyte binding agent; or ii) a population of analyte binding particles, wherein the analyte binding particles are coated with a first analyte binding agent and a second analyte binding agent;
   c) combining the test sample, the analyte binding particles, and the solid phase apparatus, thereby producing contacted analyte binding particles;
   d) maintaining the solid phase apparatus under conditions which allow contacted analyte binding particles to bind to the first sample capture reagent in the first sample capture zone, and allow contacted second analyte binding particles to bind to the second sample capture reagent in the second sample capture zone; and
   e) determining the ratio of the amount of contacted first analyte binding particles in the first sample capture zone to the amount of contacted second analyte binding particles in the second capture zone,
   wherein the ratio is equal to the relative amounts of the analytes of interest in the fluid sample.

2. The method of claim 1, wherein the application point, first sample capture zone, and second sample capture zone are sequentially located on the solid phase apparatus.

3. The method of claim 1, wherein each sample capture zone is approximately equidistant from the application point.

4. The method of claim 1, wherein the analyte binding particles are provided in a sample collection apparatus that is not in fluid communication with the solid phase apparatus, and wherein the combining of the test sample, the analyte binding particles, and the solid phase apparatus in step (c) comprises introducing the fluid test sample into the sample collection apparatus, thereby producing a mixed fluid test sample comprising contacted analyte binding particles, and applying the mixed fluid test sample to the application point of the solid phase apparatus.

5. The method of claim 2, wherein the analyte binding particles are provided in a conjugate zone that is at the application point or sequentially located between the application point and the first sample zone, and wherein the combining of the test sample, the analyte binding particles, and the solid phase apparatus in step (c) comprises applying the fluid test sample to the application point of the solid phase apparatus, and maintaining the apparatus under conditions that allow fluid to move through the conjugate zone by capillary action, thereby producing contacted analyte binding particles.

6. The method of claim 3, wherein the analyte binding particles are provided in one or more conjugate zone(s), with either a single conjugate zone at the application point, or more than one conjugate zone with a conjugate zone approximately equidistant between the application point and each sample capture zone, and wherein the combining of the test sample, the analyte binding particles, and the solid phase apparatus in step (c) comprises applying the fluid test sample to the application point of the solid phase apparatus, and maintaining the apparatus under conditions that allow fluid to move to and through each conjugate zone by capillary action, thereby producing contacted analyte binding particles.

7. The method of claim 1, wherein the solid phase apparatus is a lateral flow solid phase apparatus.

8. The method of claim 1, wherein the solid phase apparatus is a capillary flow solid phase apparatus.

9. The method of claim 1, wherein a detected background amount is subtracted prior to determining the ratio.

* * * * *